(12) United States Patent
Lipkowski

(10) Patent No.: US 8,551,939 B2
(45) Date of Patent: Oct. 8, 2013

(54) PEPTIDE ANALOGUES, PARTICULARLY FOR THE TREATMENT OF CHRONIC PAIN

(75) Inventor: Andrzej Lipkowski, Warsaw (PL)

(73) Assignee: Instytut Medycyny Doswiadczalnej I Klinicznej, Warsaw (PL)

( * ) Notice: Subject to any disclaimer, the term of this patent is extended or adjusted under 35 U.S.C. 154(b) by 0 days.

(21) Appl. No.: 12/995,606

(22) PCT Filed: Jun. 3, 2009

(86) PCT No.: PCT/PL2009/050009
§ 371 (c)(1),
(2), (4) Date: Mar. 28, 2011

(87) PCT Pub. No.: WO2009/148343
PCT Pub. Date: Dec. 10, 2009

(65) Prior Publication Data
US 2011/0166083 A1     Jul. 7, 2011

(30) Foreign Application Priority Data
Jun. 3, 2008   (PL) .......................... 385357

(51) Int. Cl.
*A61K 38/08*   (2006.01)
*A61K 38/00*   (2006.01)

(52) U.S. Cl.
USPC .......................... 514/1.1; 514/21.6

(58) Field of Classification Search
None
See application file for complete search history.

(56) References Cited

U.S. PATENT DOCUMENTS

| | | | |
|---|---|---|---|
| 2,029,881 A1 | 10/2003 | Kream | |
| 6,759,520 B1 * | 7/2004 | Carr et al. | 530/402 |
| 6,881,829 B2 * | 4/2005 | Kream | 530/402 |
| 2003/0032774 A1 * | 2/2003 | Brown et al. | 530/330 |

FOREIGN PATENT DOCUMENTS

| | | |
|---|---|---|
| EP | 2 297 179 B1 | 9/2012 |
| WO | WO 2007/100718 * | 9/2007 |

OTHER PUBLICATIONS

U.S. Appl. No. 10/542,343, filed Jan. 30, 2006 including the file history thereof.
U.S. Appl. No. 12/449,944, filed Sep. 2, 2009 including the file history thereof.
Bonney Im et al., "Spinal antinociceptive effects of AA501, a novel chimeric peptide with opioid receptor agonist and tachykinin receptor antagonist moieties", European Journal of Pharmacology, vol. 488, Apr. 1, 2004, pp. 91-99.
Bredeloux P. et al., "Interactions between NTS2 neurotensin and opioid receptors on two nociceptive responses addressed on the hot plate test in mice", Behavioural Brain Research, Elsevier, Amsterdam, NL, vol. 175, No. 2, Dec. 15, 2006, pp. 399-407.
Foran SE et al., "Inhibition of Morphine Tolerance Development by a Substance P-Opioid Peptide Chimera", The Journal of Pharmacology And Experimental Therapeutics, Jun. 1, 2000, vol. 395, No. 3, pp. 1142-1148.
Kharchenko EP et al., "Chimeras from regularoty peptides as an instrument for the analysis of their action", Doklady Akedemii Nauk SSSR, vol. 297, No. 5, May 1, 1987, pp. 1264-1267.
Kleczkowska P. et al., "Chimeric opioid-neurotensin ligands as new prospective analgesics in chronic pain" Journal of Peptide Science, vol. 14, No. 8, Suppl. S. 058, Aug. 1, 2008, pp. 157-158.
International Search Report issued by the International Searching Authority (ISA/EP) on Dec. 8, 2009 in connection with International Application No. PCT/PL2009/050009.

* cited by examiner

*Primary Examiner* — Cecilia J Tsang
*Assistant Examiner* — Sergio Coffa
(74) *Attorney, Agent, or Firm* — Gary J. Gershik; Cooper & Dunham LLP

(57) ABSTRACT

The use is claimed of opioid peptides with a novel structure, which in addition to the pharmacophore contain structural elements that interact with neurotensisn receptors. Due to the synergistic interaction with the additional element, an augmented analgesic activity is obtained, capable of being used for an extended period due to decreased drug tolerance induction. These compounds may be of particular use in the treatment of chronic pain as effective analgesics during inflammation caused by rheumatoid, gout, neurodegeneration, postoperative or post-accidental lesions, or oncogenic lesions.

12 Claims, 1 Drawing Sheet

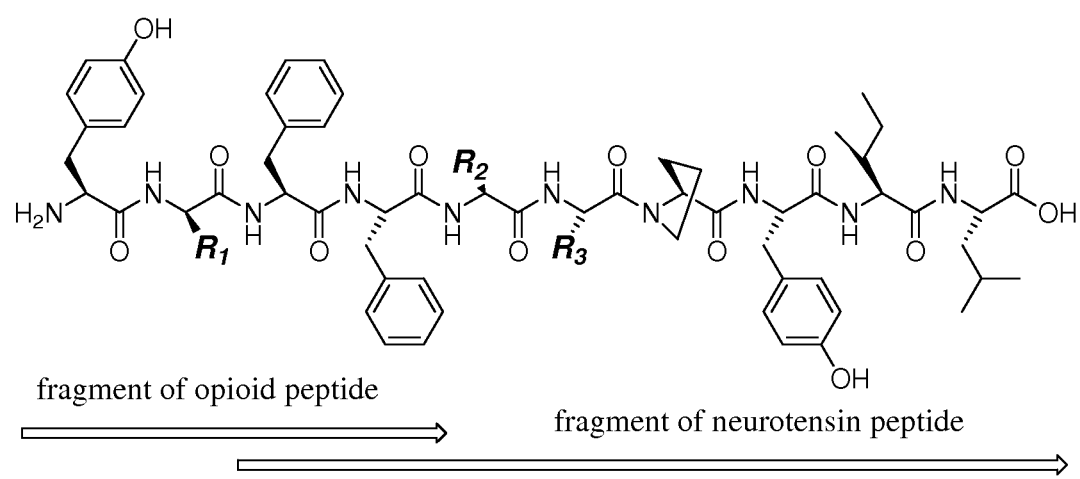

PEPTIDE ANALOGUES, PARTICULARLY FOR THE TREATMENT OF CHRONIC PAIN

This application is a §371 national stage of PCT International Application No. PCT/PL2009/05009, filed Jun. 3, 2009, and claims priority of Polish Patent Application No. PL-385357, filed Jun. 3, 2008, the contents of all of which are hereby incorporated by reference into this application.

The subject of the present invention comprises novel peptide analogues exhibiting affinity for opioid and neurotensin receptors, possessing the general formula shown FIG. 1, for peripheral or central administration in the form of an infusion, injection or implant in the treatment strong pain during rheumatoidal inflammation, post-trauma, post-surgery or oncogenic pain.

A pain signal, arising as and result of disease or tissue damage, is transmitted to the central nervous system where it generates the sensation of pain. The magnitude of the pain stimulus is regulated by the nociceptive and antinociceptive receptor system located on the nervous cell surface. Endogenous opioid peptides comprise one of the natural factors which dampen the pain signal as and result of activating antinociceptive receptors. Opioid receptors are also activated by the administration of opioid analgesics, such as morphine or phentanyl. The opioid system is but one of and wide range of natural substances and their receptors jointly regulating the transmission and modulation of pain signals. The plasticity of this system results in the fact that the long-term administration of opioid analgesics causes an adaptive remodelling of the initial neuroregulatory system of pain signal transmission, which in turn results in increased drug tolerance and dependency formation. It was determined that the endogenous neuropeptide neurotensin is involved in the transmission of pain signals. Yano K, Kimura S, Imanishi Y, 1998, "Simultaneous activation of two different receptor systems by enkephalin/neurotensin conjugates having spacer chins of various lengths.", European Journal of Pharmacological Sciences, Vol. 7, pp. 41-48 describes novel compounds in which and peptide affecting opioid receptors was connected to neurotensin via peptide bonds of various length. The hybrid compounds produced exhibited and great affinity for opioid and neurotensin receptors. Analgesis research in animals suggests and synergistic activity of the two conjugated peptides.

During research on the dependence of the biological activity on the structure of opioid peptides and neurotensin, it was unexpectedly shown that opioid peptides and neurotensin possess shared or structurally similar peptide fragments essential for and high affinity for opioid and neurotensin receptors. This research resulted in and series of new peptide analogues in which the active portion of the opioid peptide is partially shared with the neurotensin peptide. It was unexpectedly shown that the analogues possessing the general formula shown in FIG. 1 exhibit and strong affinity for opioid and neurotensin receptors. Peptides administered to experimental animals in the subarachnoid space induced and strong analgesic effect. The administration of the peptide at an analgesic dose caused no drug tolerance as is observed for morphine administered at what is initially an analgesic dose. Also unexpectedly, it was shown that the analogues possessing the general formula shown in FIG. 1 also induce and strong analgesic effect in models of chronic inflammation. The FIGURE shows and general formula of peptide analogues with an affinity for opioid and neurotensin receptors, in which $R_1$ means an amino-acid residue selected from among: D-alanine, D-threonine, D-serine, D-lysine or D-arginine, and $R_2$ and $R_3$ are identical or different and denote an amino-acid residue selected from among: lysine or arginine.

The subject of the present invention are novel peptide analogues possessing the general formula shown in FIG. 1, characterised by a high affinity for opioid as well as neurotensin receptors, involved in the transmission or modulation of pain signals, which may be of use in the treatment of chronic pain arising as a result of disease, post-operational or post-accident trauma.

In particular, the subject of the present invention are compounds selected from the group consisting of: Tyrosyl-D-lysyl-phenylalanyl-phenylalanyl-arginyl-arginyl-prolyl-tyrosyl-isoleucyl-leucine, Tyrosyl-D-arginyl-phenylalanyl-phenylalanyl-lysyl-lysyl-prolyl-tyrosyl-isoleucyl-leucine and Tyrosyl-D-lysyl-phenylalanyl-phenylalanyl-lysyl-lysyl-prolyl-tyrosyl-isoleucyl-leucine.

Next aspect of the invention is a use of the peptide according to the invention, as defined above, in the production of an analgesic drug.

Possibly, the drug produced is designed for peripheral administration or administration into the central nervous system, particularly those caused by inflammation, such as rheumatoidy, neuropathy or oncogenic states, by cancer, or rheumatoid inflammation, or gout, or multiple sclerosis, or osteoporosis, or post-operative neuropathies, or post-accident trauma, or tumour take. Particularly, the drug produced is designed to interact with neurotensin receptors.

To better illustrate the activity of the present invention consisting of the analgesic activity of compounds presented in FIG. 1, the attached examples demonstrate the effectiveness of multiple administration of the compounds in animal pain models. However, the scope of the present invention should in no way be limited to the content of the examples below.

The peptides with the general formula shown in FIG. 1 were synthesized in the solid phase according to a general synthesis scheme using the Fmoc protocol described in the monograph by W. C. Chan and P. D. White, "Moc solid phase peptide synthesis: and practical approach", Oxford University Press, Oxford, 2000. Synthesis was initiated using Moc-Leucine conjugated with a Wang-type resin via sequential decoupling of the Fmoc protectant and attachment of appropriate Fmoc-amino-acids. 99% TFA was used to detach the formed peptide from the polymer carrier. The raw peptide was purified using a two-stage process: using a molecular sieve (Sephadex LH-20), and then HPLC. Each run resulted in pure peptides as hydrochloride salts, with amino-acid analysis and mass spectroscopy results in accordance with the theoretical calculations.

EXAMPLE I

Inflammation was induced in mice by administering Freund's adjuvant into the paw. Inflammation was observed within two days. After a week, we examined the analgesic activity of the peptide analogue Tyrosyl-D-lysyl-phenylalanyl-phenylalanyl-arginyl-arginyl-prolyl-tyrosyl-isoleucyl-leucine against acute pain elicited by immersion of the tail into 55° C. Intravenous administration of the peptide analogue at a rate of 20 mg/kg caused complete analgesis in mice with inflammation.

EXAMPLE II

In an animal oncogenic pain model, in mice, inflammation was induced via the administration of about a million murine melanoma cells into the hind leg. After two days we observed increasing inflammation due to tumour take. After two weeks of tumour development we examined the effect of Tyrosyl-D-arginyl-phenylalanyl-phenylalanyl-lysyl-lysyl-prolyl-tyrosyl-isoleucyl-leucine against acute pain elicited by tail immersion in 55° C. water. Intraperitoneal administration of the peptide analogue at 30 mg/kg caused complete analgesis in mice with inflammation.

EXAMPLE III

Two weeks prior to the experiment, rats were implanted with cannulae into the subarachnoid space. On the day of the experiment we examined analgesic activity by administering the peptide Tyrosyl-D-lysyl-phenylalanyl-phenylalanyl-lysyl-lysyl-prolyl-tyrosyl-isoleucyl-leucine. A dose of 5 mg of analogue causes complete analgesis against thermal pain for 1 hour. A daily dose of 5 mg caused no changes in the extensive analgesic effect of the administered peptide.

The invention claimed is:
1. A compound with the general formula:

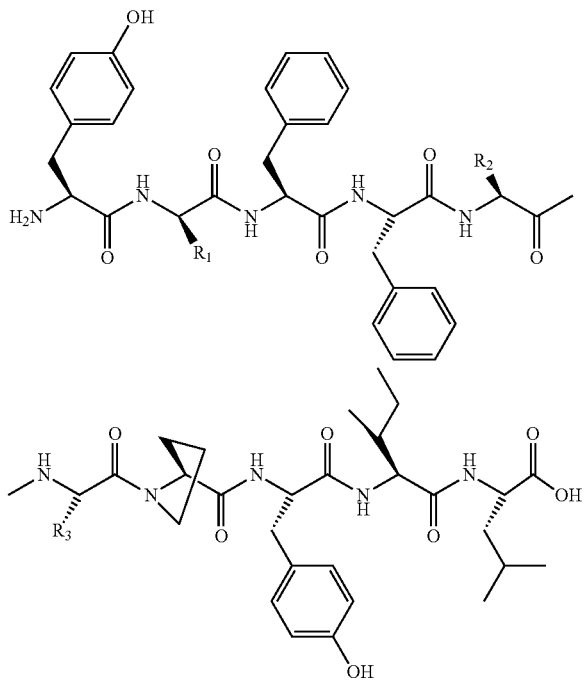

wherein $R_1$, denotes an amino-acid residue selected from the group consisting of D-alanine, D-threonine, D- serine, D-lysine or D-arginine, and wherein $R_2$ and $R_3$ are identical or different and denote amino-acid residues selected from the group consisting of lysine or arginine.

2. The compound according to claim 1 selected from the group consisting of: Tyrosyl-D-lysyl-pnenylalanyl-phenylalanyl-arginyl-arginyl-prolyl-tyrosyl-isoleucyl-leucine, Tyrosyl-D-arginyl-phenylalanyl-phenylalanyl-lysyl-lysyl-prolyl-tyrosyl-isoleucyl-leucine, and Tyrosyl-D-lysyl-phenylalanyl-phenylalanyl-lysyl-lysyl-prolyl-tyrosyl-isoleacyl-leucine.

3. The compound of claim 2, which is Tyrosyl-D-lysyl-phenylalanyl-phenylalanyl-arginyi-arginyl-prolyl-tyrosyl-isoleucyl-leucine.

4. The compound of claim 2, which is Tyrosyl-D-arginyl-phenylalanyl-phenylalanyl-lysyl-lysyl-prolyl-tyrosyl-isoleucyl-leucine.

5. The compound of claim 2, which is Tyrosyl-D-lysyl-phenylalanyl-phenylalanyl-lysyl-lysyl-prolyl-tyrosyl-isoleucyl-leucine.

6. A composition comprising the compound of claim 1 and a carrier.

7. The composition of claim 6, in the form of a venous infusion for peripheral administration, a subdermal implant, an intraperitoneal implant or a subarachnoid implant.

8. The composition of claim 6, further comprising a pharmaceutically permissable active substance.

9. The composition of claim 6, in the form of a lyophilisate.

10. The compound of claim 6, comprising a solid polymer carrier.

11. A method for treating pain in a subject comprising administering to the subject the compound of claim 1 in an amount effective to treat pain in the subject.

12. The method according to claim 11, wherein the compound interacts with neurotensin receptors.

* * * * *

UNITED STATES PATENT AND TRADEMARK OFFICE
CERTIFICATE OF CORRECTION

PATENT NO.        : 8,551,939 B2
APPLICATION NO.   : 12/995606
DATED             : October 8, 2013
INVENTOR(S)       : Andrzej Lipkowski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 74 days.

Signed and Sealed this

Fifteenth Day of September, 2015

Michelle K. Lee
*Director of the United States Patent and Trademark Office*